US011058785B1

(12) United States Patent
Spurling et al.

(10) Patent No.: US 11,058,785 B1
(45) Date of Patent: Jul. 13, 2021

(54) PORTABLE GERMICIDAL APPARATUS FOR PROVIDING UVC RADIATION

(71) Applicant: SMS Technologies, LLC, Elk River, MN (US)

(72) Inventors: Brent Edward Spurling, Sparta, WI (US); Gene Pearson, Trempealeau, WI (US)

(73) Assignee: SMS Technologies, LLC, Elk River, MN (US)

( * ) Notice: Subject to any disclaimer, the term of this patent is extended or adjusted under 35 U.S.C. 154(b) by 0 days.

(21) Appl. No.: 16/933,800

(22) Filed: Jul. 20, 2020

Related U.S. Application Data

(63) Continuation of application No. 16/946,922, filed on Jul. 10, 2020, now abandoned.

(60) Provisional application No. 62/992,052, filed on Mar. 19, 2020.

(51) Int. Cl.
*A61L 2/10* (2006.01)
*A61L 2/26* (2006.01)

(52) U.S. Cl.
CPC .............. *A61L 2/10* (2013.01); *A61L 2/26* (2013.01); *A61L 2202/11* (2013.01); *A61L 2202/16* (2013.01)

(58) Field of Classification Search
CPC ..................................... A61L 2/10; A61L 2/26
USPC ........................................ 250/454.11, 455.11
See application file for complete search history.

(56) References Cited

U.S. PATENT DOCUMENTS

| 5,601,786 A | 2/1997 | Monagan |
| 5,656,242 A | 8/1997 | Morrow et al. |
| 5,920,075 A * | 7/1999 | Whitehead ................ A61L 2/10 |
| | | 250/492.1 |
| 6,053,968 A | 4/2000 | Miller |
| (Continued) | | |

FOREIGN PATENT DOCUMENTS

EP          2891205 B1      11/2016

OTHER PUBLICATIONS

Smith, Verilux CleanWave Portable UV Sanitizing Travel Wand Review, Sep. 17, 2018, UVHero, accessed at <https://uvhero.com/verilux-cleanwave-portable-uv-sanitizing-travel-wand-review/#:~:text=Kills%20up%20to%2099.9%20percent,of%20the%20UV%2DC%20light.>. (Year: 2018).*

(Continued)

*Primary Examiner* — Jason L McCormack
(74) *Attorney, Agent, or Firm* — Carlson, Caspers, Vandenburgh & Lindquist, P.A.

(57) ABSTRACT

Provided is a portable germicidal apparatus that is, in one embodiment, configured to be moved during operation that can comprise: a frame comprising a base, a distal end, and an elongated structural support member defining a longitudinal axis, wiring providing electrical power to the base and the distal end, wherein the apparatus is configured to permit germicidal UVC radiation to be emitted from the apparatus in a direction orthogonal to the longitudinal axis between the base and the distal end in substantially 360 degrees. A further embodiment of the present invention is described that includes a portable germicidal apparatus comprising a harness configured to be worn by a user of the apparatus, a wand configured to provide UVC radiation, and a free-range motion component that connects the harness and wand, (Continued)

supports the weight of the wand, and provides at least two degrees of freedom for movement of the wand.

20 Claims, 6 Drawing Sheets

(56) References Cited

U.S. PATENT DOCUMENTS

| | | | |
|---|---|---|---|
| 6,630,105 B1 | 10/2003 | O'Neill et al. | |
| 7,211,813 B2 | 5/2007 | Jensen | |
| 7,626,187 B2 | 12/2009 | Younts | |
| 9,265,850 B2 | 2/2016 | Davis et al. | |
| 10,195,298 B2 | 2/2019 | Reitenberg | |
| 10,583,212 B2 | 3/2020 | Ufkes | |
| 2008/0260601 A1* | 10/2008 | Lyon | B01D 53/007 422/186.3 |
| 2010/0061887 A1* | 3/2010 | Harper | A61L 2/10 422/24 |
| 2010/0104471 A1* | 4/2010 | Harmon | A61L 2/10 422/24 |
| 2014/0119986 A1* | 5/2014 | Finke | A61L 2/10 422/22 |
| 2016/0074546 A1* | 3/2016 | Rizzone | A61L 2/26 250/455.11 |
| 2016/0175896 A1* | 6/2016 | Montgomery | A47L 23/00 250/454.11 |
| 2018/0207303 A1* | 7/2018 | Farren | A61L 2/10 |
| 2020/0179543 A1* | 6/2020 | Deshays | A61L 2/24 |
| 2020/0215214 A1* | 7/2020 | Rosen | A61L 2/24 |

OTHER PUBLICATIONS

Smith, Verilux CleanWave Portable UV Sanitizing Travel Wand REveiw, Sep. 17, 2018, UVHERO, accessed at,https://uvhero.com/verilux-cleanwave-portable-uv-sanitizing-travel-wand-review#.-text=Kills%20up%20to%2099.9%20percent,of%20the%20UV%2DC%20light.>. (Year: 2018).*

FLYCAM Comfort-Stabilizing Arm & Vest for FLYCAM 5000/3000/DSLR Nano Handheld Camera Video Steadycam Stabilizer up to 7kg | Stabilization Body Mount System or camcorders Stabilization (CMFT-AV) accessed at https://www.amazon.com/Stabilizing-Stabilizer-Stabilization-camcorders-CMFT-AV/dp/B00M6PO5RQ/ref=pd_sbs_1?pd_rd_w=E2Vsi&pf_rd_p=b65ee94e-1282-43fc-a8b1-8bf931f6dfab&pf_rd_r=7JVZ4QZ2H4VZ86K8EBB88&pd_rd_r=f744455c-f1b1-4793- , Nov. 3, 2020.

FLYCAM Galaxy Dual Arm and Vest Body Mounted Steadycam for Handheld Stabilizer for Video Camera Camcorder up to 10kg/22lbs (GLXY-AV), accessed at https://www.amazon.com/FLYCAM-Steadycam-Stabilizer-Camcorder-GLXY-AV/dp/B00JBZIJMG/ref=pd_sbs_3?pd_rd_w=E2Vsi&pf_rdp=b65ee94e-1282-43fc-a8b1-8bf931f6dfab&pf_rd_r=7JVZ4QZ2H4VZ86K8EBB8& pd_rd_r=f744455c-f1b1-4793-b169-8abd04b86034&pd_rd_wg=4bMU9&pd_rd_i=B00JBZIJMG, Nov. 3, 2020.

* cited by examiner

PORTABLE GERMICIDAL APPARATUS FOR PROVIDING UVC RADIATION

CROSS-REFERENCE TO RELATED APPLICATIONS

This application is a continuation of U.S. application Ser. No. 16/946,922, filed Jul. 10, 2020, entitled "PORTABLE GERMICIDAL APPARATUS FOR PROVIDING UVC RADIATION", which claims priority to U.S. Provisional Application No. 62/992,052, filed on Mar. 19, 2020, entitled "ULTRAVIOLET GERMICIDAL SYSTEMS", the contents of which are hereby incorporated herein by reference.

BACKGROUND

There exists a need to eradicate and/or inhibit the growth or action of microorganisms. Ultra-Violet light with wavelengths in the 100-280 nm range, called UVC, is a known to have germicidal qualities. As a result of evolving bacterial, viral, and other pathogenic sources, such as the COVID-19 coronavirus pandemic, there is a need for improved methods and apparatuses for broadcasting UV-C light. The system of the present invention is not subject to the disadvantages of systems known in the prior art and possess many advantages not found in known systems.

SUMMARY OF THE INVENTION

The present invention generally relates to portable germicidal apparatuses for providing UVC radiation. In accordance with the present invention, apparatuses are constructed to allow the convenient distribution of germicidal UVC light to sterilize and/or reduce pathogenic loads on and/or within surfaces and substances. In accordance with another aspect of the present invention, a user-worn harness provides support and stability to the operation of a portable, germicidal UVC wand.

One aspect of the invention is a portable germicidal apparatus. The apparatus includes a frame. The frame includes a base, a distal end, and a structural support member. The base includes a first lamp holder for holding a first end of at least one elongated UVC lamp. The distal end includes a second lamp holder for holding a second end of the at least one elongated UVC lamp. The structural support member connects the base and distal end and defines a longitudinal axis. The apparatus further includes wiring providing electrical power to the base and distal end. The apparatus is configured to hold one or more UVC light sources that emit germicidal UVC radiation from the apparatus in a direction orthogonal to the longitudinal axis in substantially 360 degrees. The apparatus is further configured to be moved during operation.

Another aspect of the invention is a portable germicidal apparatus that includes a harness, a wand, and a free-range motion component. The harness is configured to be worn by the user of the apparatus. The wand is configured to emit UVC radiation. The free-range motion component connects the harness and the wand, supports the weight of the wand, and provides at least two degrees of freedom for movement of the wand.

Another aspect of the invention is a portable germicidal apparatus that includes a harness, a wand, and a free-range motion component. The harness is configured to be worn by the user of the apparatus. The wand includes a frame. The frame includes a base, a distal end, and a structural support member. The base includes a first lamp holder for holding a first end of at least one elongated UVC lamp. The distal end includes a second lamp holder for holding a second end of the at least one elongated UVC lamp. The structural support member connects the base and distal end and defines a longitudinal axis. The wand further includes wiring providing electrical power to the base and distal end. The wand is configured to permit one or more UVC light sources to emit germicidal UVC radiation from the apparatus in a direction orthogonal to the longitudinal axis in substantially 360 degrees. The free-range motion component connects the harness and the wand, supports the weight of the wand, and provides at least two degrees of freedom for movement of the wand. In some particular embodiments, it can provide at least three degrees of freedom for movement of the wand. In some embodiments, it can provide at least four degrees of freedom for movement of the wand.

In another aspect of the invention, the apparatus includes at least three or four lamp holders at both the base and distal end for holding at least three or four elongated lamps. In some embodiments these elongated lamps can be positioned radially outward of the longitudinal axis and permit the lamps to collectively emit UVC radiation from the apparatus in a direction orthogonal to the longitudinal axis in substantially 360 degree. This can be accomplished without the use of reflectors.

In another aspect of the invention, the apparatus can include a housing configured to protect the at least one ultraviolet lamp. This housing can be made using a substantially transparent material and/or it can have a cage design. The apparatus can also include a central support member along the longitudinal access and one or more supports disposed between the base and the distal end. The supports can be oriented orthogonal to the longitudinal axis and include openings capable of allowing one or more lamps to extend therethrough.

In another aspect of the invention the free-range motion component can include at least three joint structures, each providing for rotation around at least two axes. In another aspect of the invention, a spring can be provided between the first and second joint structure and/or between the second and third joint structure. Such springs can be configured to reduce the force needed to move the wand while also maintaining adequate tension to provide stability to the position of the wand. The free-range motion component can also include fasteners, such as handles that can be rotated to loosen and tighten a tensioning bolt, that can be adjusted to increase or reduce the amount of force needed to move the wand in a particular direction or plane and/or to prevent motion of the wand in a particular direction or plane.

The above summary of the present invention is not intended to describe each illustrated embodiment or every implementation of the present invention. The following figures and detailed description more particularly exemplify these embodiments.

BRIEF DESCRIPTION OF THE DRAWINGS

The invention may be more completely understood in consideration of the following detailed description of various embodiments of the invention in connection with the accompanying drawings, in which.

The invention is amenable to various modifications and alternative forms, and specifics thereof have been discussed by way of example. It should be understood that the invention is not limited the invention to the particular embodiments described. On the contrary, the invention extends to all modifications, equivalents and alternatives falling within the spirit and scope of the invention as defined by the appended claims.

DETAILED DESCRIPTION

Figure 1:
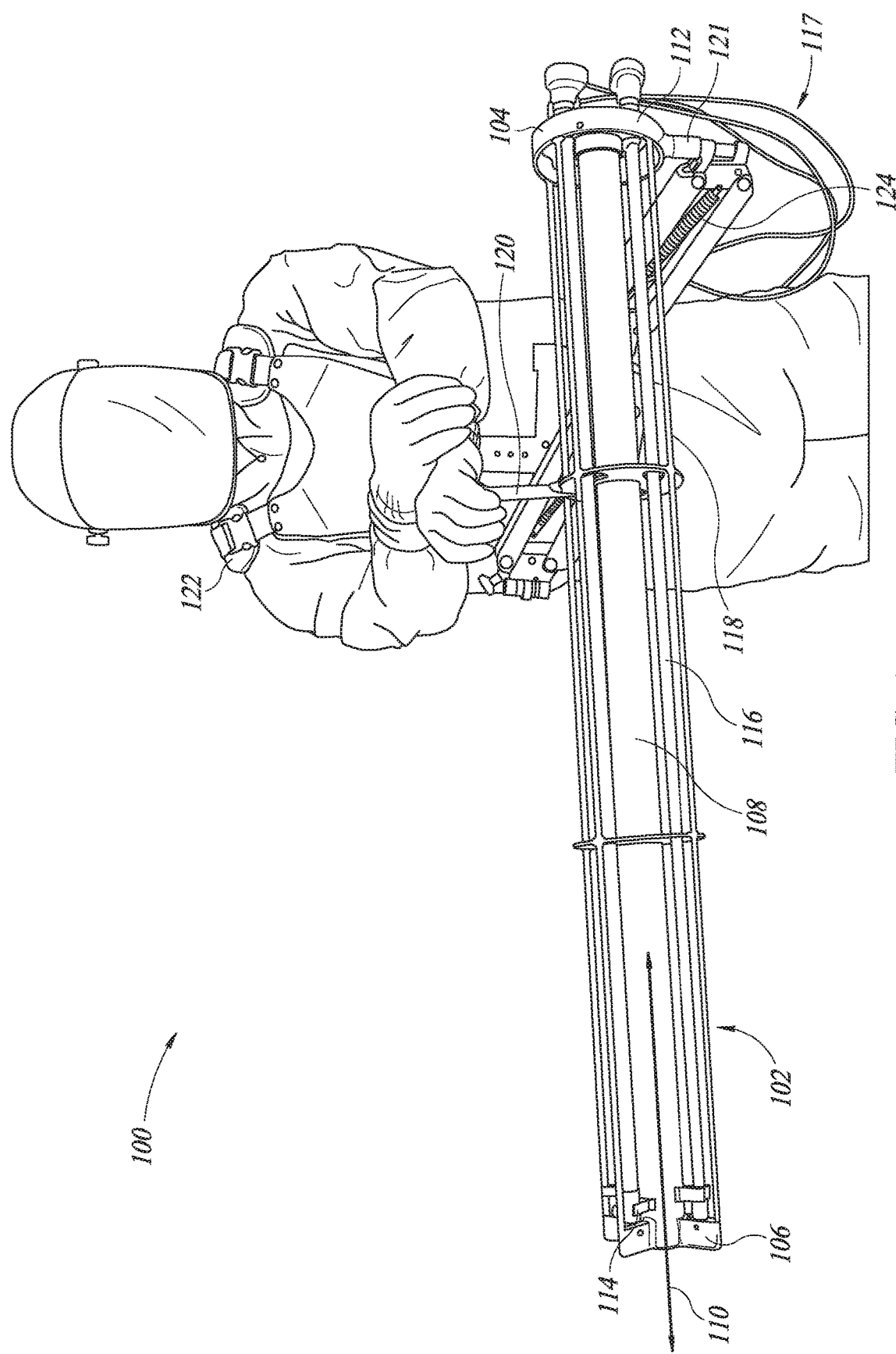
FIG. 1 shows an embodiment of the portable germicidal apparatus of the present invention.

FIG. 1 depicts an exemplary embodiment of portable germicidal apparatus 100. As shown by FIG. 1, apparatus 100 comprises a wand 102. Wand 102 has a frame with a base 104 and a distal end 106. The base 104 and distal end 106 are preferably separated by about 12-80 inches. They can be separated by any suitable amount. In one embodiment, the base 104 and distal end 106 can be separated by about 12 inches. In other embodiments they can be separated by 24 inches, 36 inches, 50 inches, and 61 inches.

Wand 102 also includes a central support member 108 that defines a longitudinal axis 110. Wand 102 includes base lamp holders 112 and distal lamp holders 114. These lamp holders are shown holding elongated UVC lamps 116. Lamp holders 112 and 114 can be any suitable means for holding and providing power to UVC lamps 116. For example, lamp holders 112 and 114 can hold the UVC lamps 116 using clamps, sockets, snap in mechanisms, spring loaded mechanisms, or bi-pin mechanisms. The illustrated embodiment in FIG. 1 includes four UVC lamps 116, but more or fewer UVC lamps could be used. For example, in some embodiments the frame could hold any number of lamps, including as few as one or as many as 16 lamps. While reference is made throughout this specification to UVC lamps, any other forms of UVC light sources could also be used. The lamps can be placed at equal distances from the central support member and from adjacent lamps, such as in a circular pattern surrounding the central support member. As an alternative, the lamps can be divided into two sets with each set being located a different distance from the central support member. For example, the first, third, fifth, and seventh lamps could be located a first distance, while the second, fourth, sixth, and eighth lamps could be located a second distance from the central support member. This arrangement would permit the use of more bulbs in a smaller volume, thereby reducing the size of the wand.

Wand 102 also includes wiring 117 that supplies electrical power to the base lamp holders 112 and distal lamp holders 114. In the illustrated embodiment in FIG. 1, the wiring 117 goes through an internal chamber in the central support member 108 to reach the distal lamp holder 114. The wiring can reach the distal lamp holder in any other suitable way as well, such as by being attached to the housing or by freely attaching to the distal end.

Wand 102 can also include a housing or housing members 118. The housing members 118 in the illustrated embodiment in FIG. 1 are bars that serve to protect the bulbs from contact during movement of the wand. Alternatively, the housing can have a cage design or can be a housing made of a substantially transparent material. The cage or substantially transparent housing can optionally be supported by one or more housing support members 118. The housing can be substantially cylindrical. The housing can be any suitable size. In one preferred embodiment, the diameter is 18 inches.

The apparatus can also be provided with one or more handles. For example, a handle 120 can be attached to wand 102. This handle can be any suitable shape and size to allow the user to control and move the wand. Alternatively, or in addition, a handle 121 can be provided at a position near or on the base 104 of the wand 102. In yet another alternative, the wand 102 is provided with two handles, e.g., handles 120 and 121, located at different locations along the longitudinal axis of the wand to facilitate positioning of the wand. In other embodiments the handles can be in different locations, have different orientations, and be made of different materials. In some embodiments the handles are adapted such that the wand can be easily and comfortably held and operated by the user without the use of the below identified harness. Such an arrangement could involve the use of three or more handles distributed along the length of the wand. There can also be one or more additional handles designed for purposes of picking up and setting down the wand (as opposed to operation of the wand).

The portable germicidal apparatus 100 also can include a harness 122 that can be worn by the user of the apparatus. While the embodiment of the harness illustrated embodiment in FIG. 1 includes straps that go over the user's shoulders that are connected in the front at the chest (and can also be connected in the back to help distribute the load of the wand), the harness of the present invention can take any suitable form including, for example, a backpack, a belt, a shoulder sling, or a yoke.

The portable germicidal apparatus 100 also includes a free-range motion component 124 that connects the wand to the harness. The details of the free-range motion component 124 will be discussed in more detail in relation to FIGS. 3 and 4.

Wiring connected to a power source can also be guided through the harness 122 and the free-range motion component to the wand in order to provide power to the lamp holders on the base and distal ends. Attached to the wiring between the power source and the lamps there can be one or more ballasts. These ballasts can be located in a power box, which can be contained by the harness, carried in a user's hand, or rest on a cart that the user can move around a room during operation of the wand. The power box could also be attached to the user's body by any suitable means, such as in a backpack. In an alternative embodiment, the ballasts can be located inside the central support member. In this embodiment the central support member serves as the power box.

In the portable germicidal apparatus 100, UVC radiation can be emitted from the wand 102 in a direction orthogonal to the longitudinal axis in substantially 360 degrees. The portable germicidal apparatus 100 can preferably emit radiation at a distance of about 12 inches from the lamp at an amount of about 5000-10,000 $\mu W/cm^2$, more preferably about 6,000-8,000 $\mu W/cm^2$, and most preferably about 6800 $\mu W/cm^2$. The apparatus can preferably provide UVC radiation to a surface about 10 inches from the lamp at an amount of about 8,000-13,000 $\mu W/cm^2$, more preferably about 10,000-12,000 $\mu W/cm^2$, and most preferably about 10,900 $\mu W/cm^2$. A surface about 4 inches from the lamp preferably receives radiation at an amount about 20,000-25,000 μW/cm², more preferably about 21,000-23,000 μW/cm², and most preferably about 22,000 μW/cm. A surface about 2 inches from the lamp preferably receives radiation at an amount of about 35,000-45,000 μW/cm², more preferably about 39,000-42,000 μW/cm², and most preferably about 40,800 μW/cm².

Preferably the apparatus provides for significant germicidal properties at least 8 inches from the longitudinal axis, more preferably at least 10 inches, and most preferably at least 12 inches.

Figure 2A:
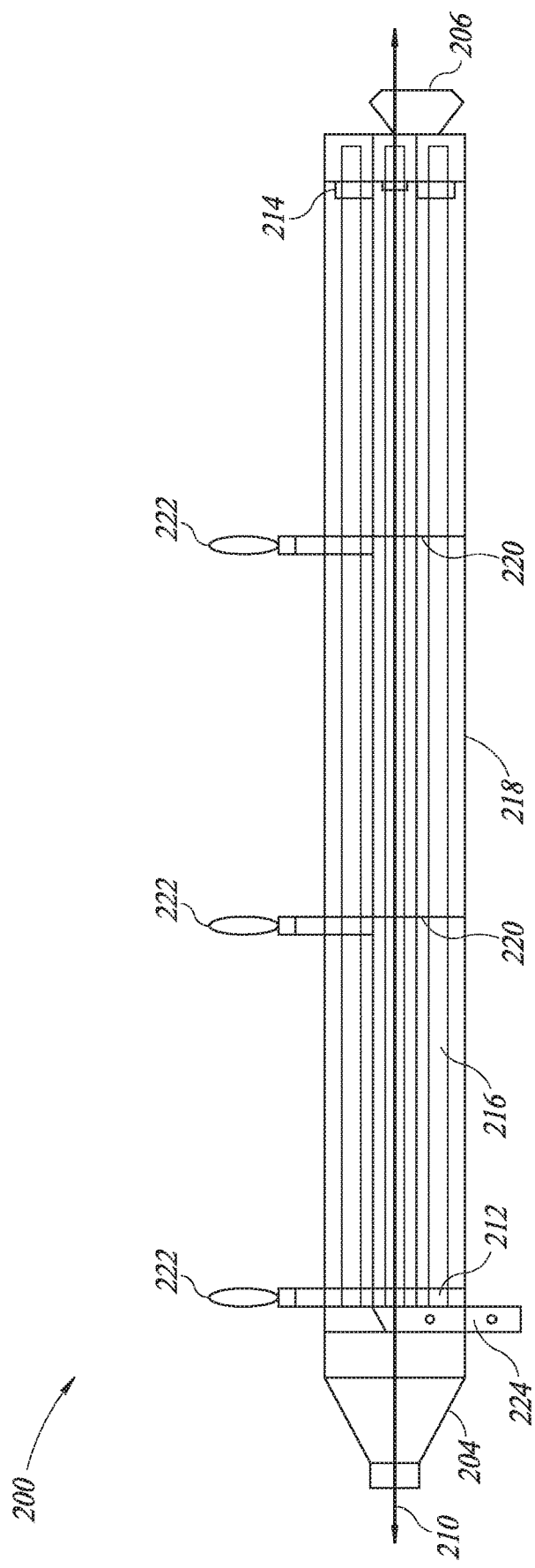
FIG. 2a is a schematic view of an embodiment of the portable germicidal apparatus of the present invention.

An exemplary embodiment of a wand 200 is schematically illustrated in FIG. 2a. Wand 200 has a frame with a base 204 and a distal end 206. In the example of wand 200, base 204 has a generally conical shape, but the base of the wand can have any shape. Wand 200 has a longitudinal axis 210. Wand 200 can include base lamp holders 212 and distal lamp holders 214. These lamp holders 212, 214 can hold elongated UVC lamps 216. Wand 200 includes housing 218. Wand 200 also includes supports 220 disposed between the base and the distal end oriented orthogonal to the longitudinal axis. Supports 220 will be discussed further in relation to FIG. 2c. In the embodiment shown in FIG. 2, wand 200 includes three handles 222 for manipulating the wand during operation. Wand 200 can also include wand mount 224 which serves to facilitate connection of wand 200 to any suitable device to be controlled by the user. For example, wand mount 224 could attach wand 200 to free range motion component 124. The connection mount can be, for example, a pole that can be placed inside a cylinder or ring connected to a free-range motion component or harness. It could also be another connection means, such as a bolt that is fastened into the free-range motion component or wand. Wand mount 224 can allow the wand to be moved relative to the device the wand is attached to. As just one example, wand mount 224 can be inserted into a pivot block that allows the wand to pivot on a horizontal plane relative to the device it is attached to. Alternatively, wand mount 224 can be designed to maintain the wand in a position fixed relative to the device the wand is attached to. In yet another embodiment, the wand mount permits fastening of the connection so that the user can choose whether to provide for movement about an axis at the connection or to maintain the wand and the device to which it is connected in a relatively fixed position. However, it is understood that the wand can also be used without being mounted on a free-range motion component or other structure.

Figure 2B:
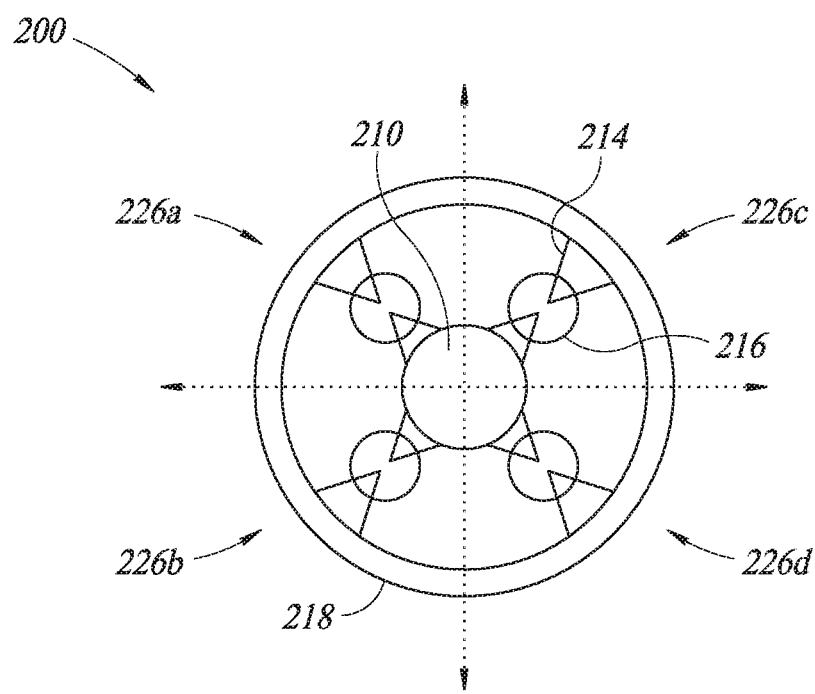
FIG. 2b is a schematic distal end view of an embodiment of the portable germicidal apparatus of the present invention.

A schematic end view of the distal end of wand 200 is shown in FIG. 2b. This end view illustrates the location of the elongated UVC lamps 216 relative to the longitudinal axis 210. Each of the four elongated UVC lamps 216 is located radially outward of the longitudinal axis 210. The housing 218 is further positioned radially outward of the UVC lamps 216, protecting the lamps from damage. In this embodiment, the wand 200 has four quadrants 226a, 226b, 226c, 226d. In this embodiment each quadrant 226a-d contains one elongated UVC lamp 216. The center of the UVC lamps 216 are preferably located about 0.5-10 inches away from the longitudinal axis, more preferably about 1-8 inches, and even more preferably about 2 inches.

Figure 2C:
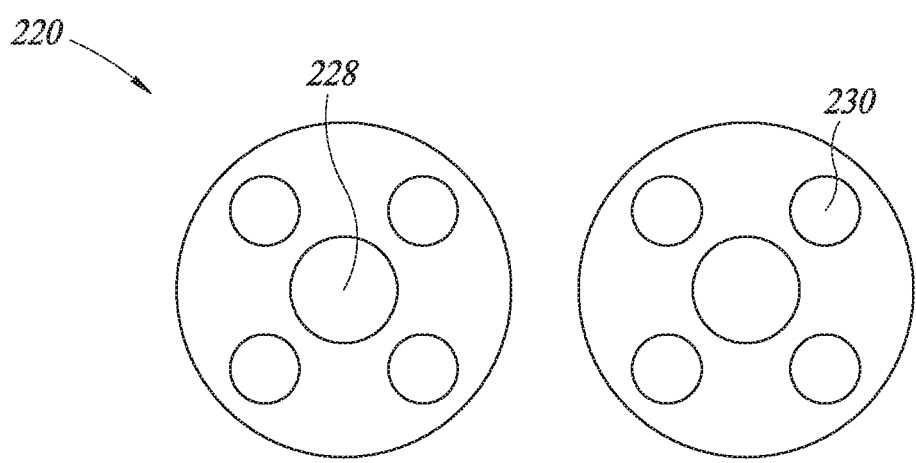
FIG. 2c is a schematic view of supports which can be used in the present invention.

FIG. 2c shows a schematic view of lamp supports 220. Lamp supports 220 each include a central opening 228 through which a central support member can extend. They each also include one or more lamp openings 230 capable of allowing a lamp to extend therethrough. They can be provided with padding or other contacts to engage and support the UVC lamp.

Figure 3:
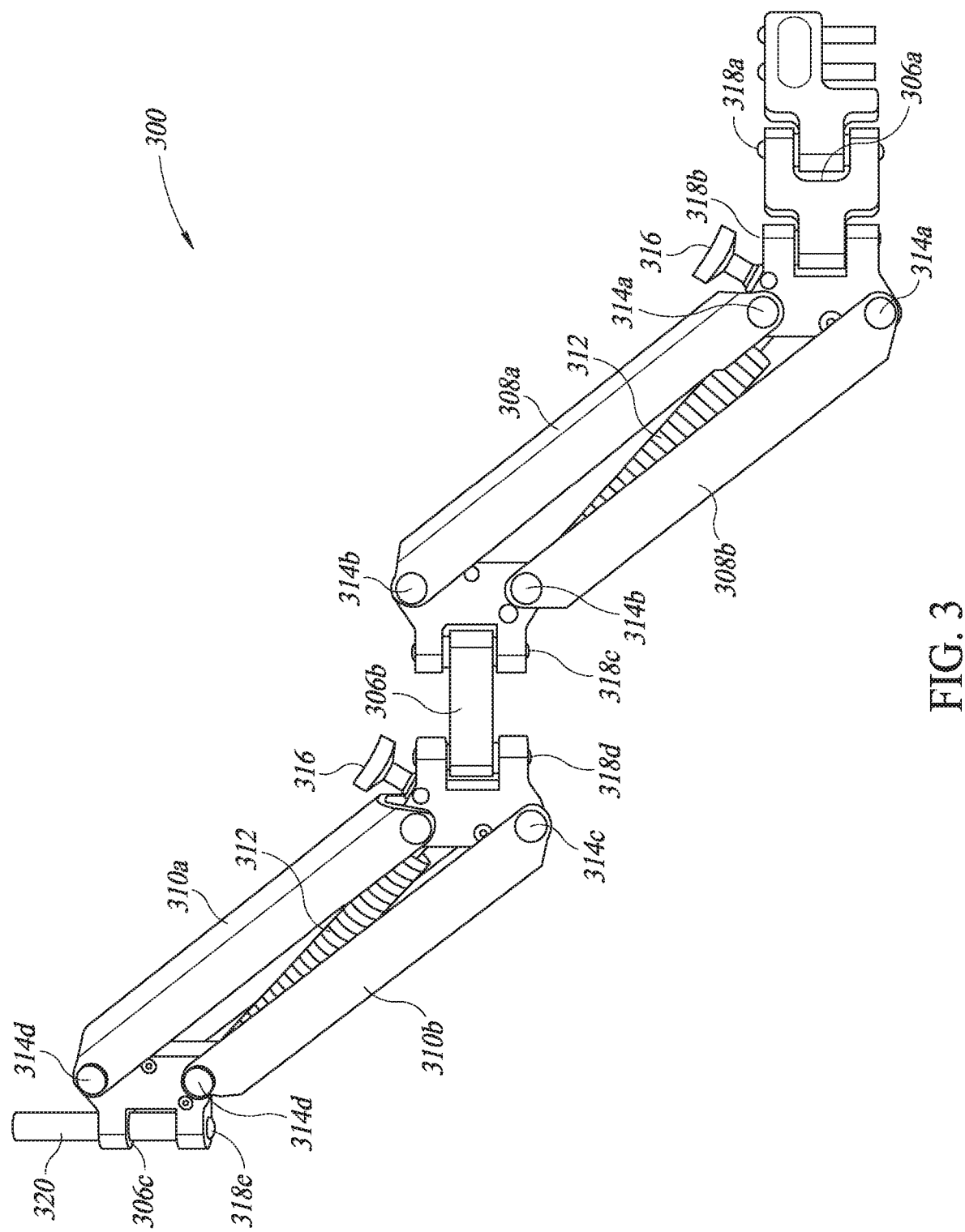
FIG. 3 shows an embodiment of a free-range motion component in accordance with the present invention.
Figure 5:
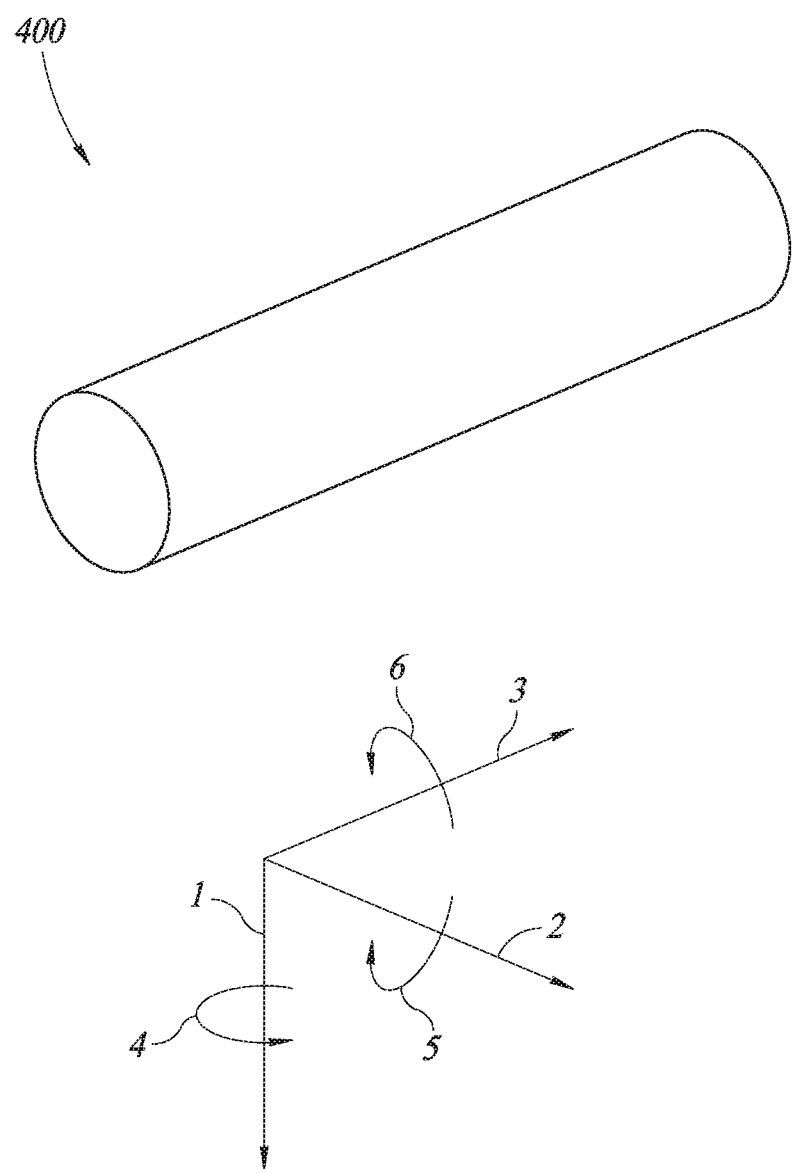
FIG. 5 illustrates the six (6) possible degrees of freedom in movement of a wand.

An exemplary embodiment of free-range motion component 300 in accordance with the present invention is shown in FIG. 3. This free-range motion component 300 connects a wand to a harness and allows the user to move the wand with five degrees of freedom. For the purposes of this patent "degrees of freedom" shall mean number of independent parameters that define the wand's motion in space. As shown in FIG. 5, A rigid body can have up to six degrees of freedom (1) vertical (elevating/heaving); (2) sideways (strafing/swaying); (3) forward and backward (walking/surging); (4) swiveling left and right (yawing); (5) tilting forward and backward (pitching); and (6) rotating (rolling). The free-range motion component 300 allows the wand to have as many of these degrees of freedom as desired.

Free-range motion component 300 can include joint structures 306 such as the three joint structures 306a, 306b, 306c shown in FIG. 3. Joint structures 306 can provide for movement in at least one direction by forming a joint with rigid members 308 and 310. For example, between joint structure 306a and 306b, there can be a top rigid member 308a, a bottom rigid member 308b, and a spring 312. Rigid members 308 can be joined to the joint structure through the use of pins 314 that allow rigid members 308 to pivot around the axes of the pins. The same components can be provided between joint structure 306b and 306c Each joint structure 306 can provide for movement of the wand in another direction through the use of one or more additional joints 318 within the joint structure. In the illustrated embodiment of FIG. 3, joint 306a allows rotation around two vertical axes at joints 318a and 318b, and when combined with adjacent pins 314a also allows for adjacent rigid members 308a and 308b to rotate around horizontal axes. Joint 306b also allows rotation around two vertical axes at joints 318c and 318d, and allows rigid member pairs 308a/308b and 310a/310b to rotate around horizontal axes. Joint 306c contains a mounting post 320 to which the wand can be attached and allows the wand to rotate around one vertical axis. Through use of pins 314d, joint 306c can also provide for rotation around horizontal axes relative to rigid members 308b, 310b. These use of these joint structures, optionally including a joint formed between a joint structure and one or more rigid members, can allow the free-range motion component to provide as many degrees of freedom as desired. While the figures show the use of pin/cylindrical joints, the use of other types of joints, such as ball/spherical joints, prismatic joints, etc., as well as the combination of such joints, is also within the scope of the invention.

When used, the springs between the rigid components can serve to reduce the force needed to move the wand in a particular direction. The tension on a spring can be adjusted with a fastener 316, such as a knob connected to a threaded bolt that serves to increase or decrease the length to which the spring is extended. Under such an arrangement, by tightening or loosening the fastener 316 the wand can then be more or less easily moved in a particular direction. The free-range motion component can also be provided with locks, such as a locking pin, that prevent movement of the wand in a particular direction.

Figure 4:
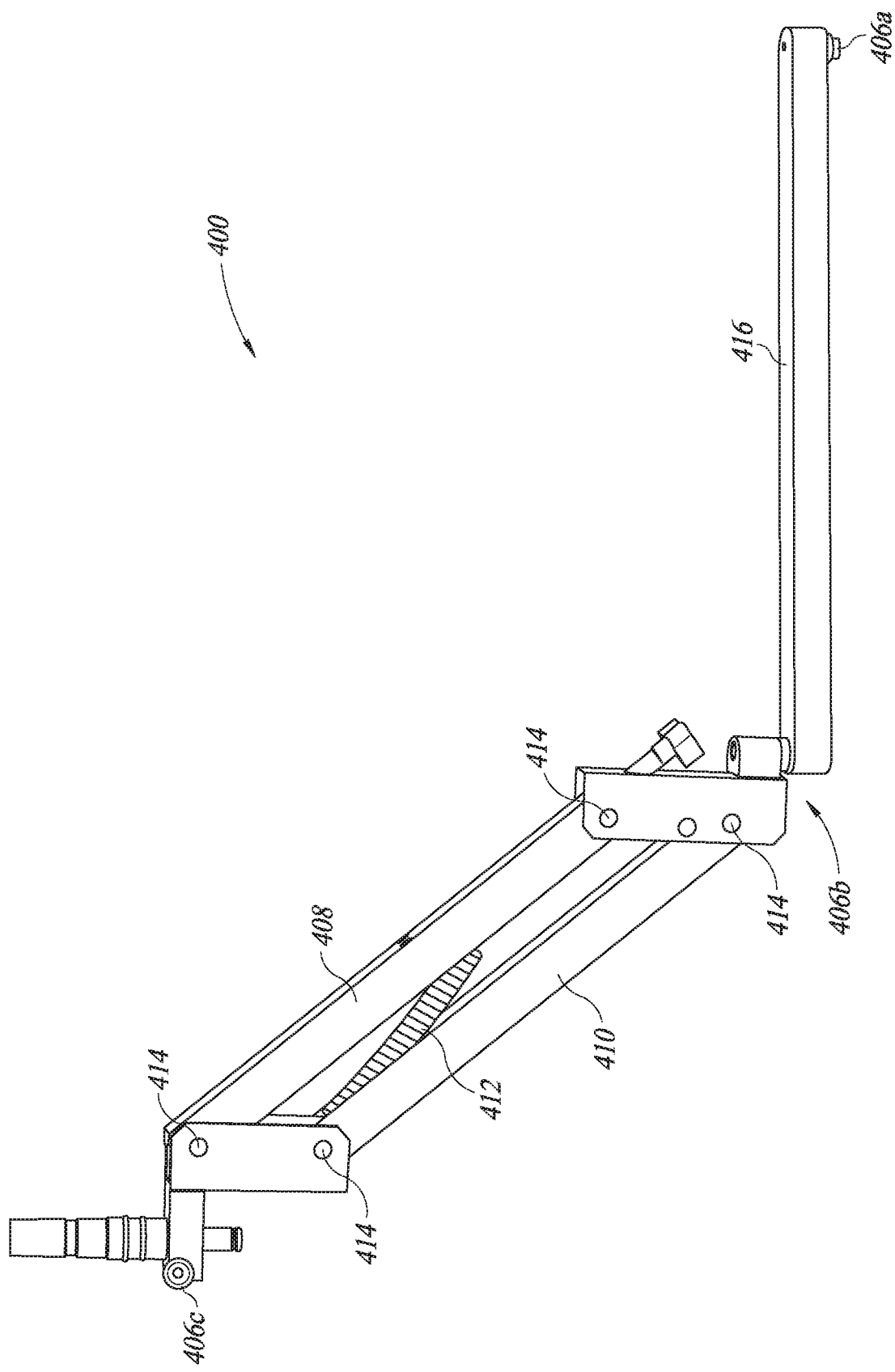
FIG. 4 shows another embodiment of a free range motion component in accordance with the present invention.

An alternative embodiment of a free-range motion component 400 is shown in FIG. 4. In this embodiment there are still three joint structures 406a, 406b, 406c but each joint structure allows rotation around only one vertical axis. Between joint structures 406b and 406c, this embodiment includes rigid structures 408 and 410, spring 412, and pins 414 that work by the same mechanism as discussed with respect to rigid members 308a/308b, spring 312, and pins 314 from FIG. 3. Between joint structures 406a and 406b, however, this embodiment includes only one rigid member 416. Although both embodiments discussed herein include three joint structures, the invention should not be considered to be limited to this number of joint structures. A free-range motion component of the present invention could have one joint structure, two joint structures, three joint structures, four joint structures, or more.

In an alternative embodiment the wand can include an integrated support brace or stand, such as one or two bipods or tripods, that can be used to station the wand on a surface without the user actively holding the wand (i.e., at a fixed location). This allows for the operator to set the apparatus down and allow it to provide germicidal UVC radiation even when it is not being moved or held by the user. Alternatively, a separate stand can be provided that is configured to hold the wand in place for irradiation from a fixed location.

In yet another embodiment the apparatus can be used in connection with an air cleaner stand. This air cleaner stand includes a tube, box, or other housing that at least the UVC-emitting portion of the wand can be placed inside and that blocks the emission of any UVC light outside of the container. The air stand cleaner can also be provided with one or more fans that serve to move air through the housing of the air cleaner stand. The fans can be located anywhere within the housing, such as near the base, around the circumference of the wand, and/or as part of a top to the housing. When the wand is placed inside the air cleaner stand and the fan(s) and wand are turned on, air is moved through the housing and subjected to UVC radiation, thereby sterilizing and/or has reducing the pathogenic load of the air.

In an additional alternative embodiment, the wand can include on or more reflectors which reflect UVC light in order to concentrate UVC radiation in a particular direction or location. Reflectors can also be used to protect the user from the UVC radiation.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

What is claimed is:

1. A user-held germicidal apparatus comprising:
   a frame comprising a base, a distal end, and a central support member; wherein
   the base comprises a first lamp holder for holding a first end of at least one elongated UVC lamp;
   the distal end comprises a second lamp holder for holding a second end of at least one elongated UVC lamp, and
   the central support member connects the base and distal end and defines a longitudinal axis along the center of the apparatus;
   a carrying component designed to permit the user to carry the apparatus during emission of UV radiation selected from the group comprising a handle, harness mount, or a combination thereof;
   wiring providing electrical power to the base and distal end;
   wherein the apparatus is configured to permit germicidal UVC radiation to be emitted from the apparatus in a direction orthogonal to the longitudinal axis in substantially 360 degrees; and
   wherein the base, distal end, and central support member are configured to be moved during emission of UVC radiation.

2. The apparatus of claim 1 wherein each of the base and distal end comprise at least four lamp holders for holding at least four elongated UVC lamps.

3. The apparatus of claim 2 wherein the apparatus is configured to hold the elongated UVC lamps positioned radially outward of the longitudinal axis and permit said four lamps to collectively emit UVC radiation from the apparatus in a direction orthogonal to the longitudinal axis in substantially 360 degrees.

4. The apparatus of claim 1 further comprising a housing configured to protect the at least one ultraviolet lamp.

5. The apparatus of claim 4 wherein the housing is substantially transparent.

6. The apparatus of claim 4 wherein the housing has a cage design.

7. The apparatus of claim 1 wherein a surface located about 12 inches from the lamp receives irradiance of least about 6800 $\mu W/cm^2$.

8. The apparatus of claim 1 wherein the distance between the base and the distal end is about 36 to about 50 inches.

9. The apparatus of claim 1 wherein the apparatus further comprises a mount near the base of the wand that can be coupled with a harness to support the apparatus.

10. The apparatus of claim 3 wherein the four UVC lamps are about 0.5 to about 4 inches from the central support member.

11. The apparatus of claim 3 further comprising:
    a housing radially outward of the at least four UVC lamps;
    one or more supports disposed between the base and the distal end, wherein the supports are oriented orthogonal to the longitudinal axis and include openings capable of allowing the one or more lamps to extend therethrough.

12. The apparatus of claim 11 further comprising a handle positioned outside of the housing and between the base and the distal end.

13. The apparatus of claim 12 comprising a second handle connected to the base.

14. A portable germicidal apparatus comprising:
    a harness configured to be worn by on at least one of the shoulder(s), torso, waist or hip(s) of a user of the apparatus;
    a wand configured to provide UVC radiation; and
    a free-range motion component that connects the harness and wand, contains at least one rigid member, allows the harness to support the weight of the wand during emission of UVC radiation, and provides at least two degrees of freedom for movement of the wand during emission of UVC radiation.

15. The apparatus of claim 14 wherein the free-range motion component comprises at least three joint structures each providing for rotation around at least one axis.

16. The apparatus of claim 15 wherein the free-range motion component comprises a first spring located between the first joint structure and the second joint structure, and a second spring located between the second joint structure and third joint structure, wherein the tension of the first and second springs can be adjusted to reduce the force needed vertically move the wand.

17. The apparatus of claim 14 wherein the free-range motion component provides at least three degrees of freedom for movement of the wand.

18. A germicidal apparatus comprising:
a harness configured to be worn on at least one of the shoulder(s), torso, waist or hip(s) of a user of the apparatus;
a wand comprising:
  a frame comprising a base, a distal end, and a central support member; wherein
  the base comprises a first lamp holder for holding a first end of at least one elongated UVC lamp;
  the distal end comprises a second lamp holder for holding a second end of at least one elongated UVC lamp, and
  the central support member connects the base and distal end and defines a longitudinal axis along the center of the apparatus;
wiring providing electrical power to the base and distal end;
  wherein the wand is configured to permit germicidal UVC radiation to be emitted from the apparatus in a direction orthogonal to the longitudinal axis; and
a free-range motion component that connects the harness and wand, allows the harness to support the weight of the wand during emission of UVC radiation, contains at least one rigid member, and provides at least two degrees of freedom for movement of the wand during emission of UVC radiation.

19. The portable germicidal apparatus of claim 18 wherein the wand is configured to permit germicidal UVC radiation to be emitted from the apparatus in a direction orthogonal to the longitudinal axis in substantially 360 degrees.

20. The portable germicidal apparatus of claim 18 further comprising one or more shields to at least partially shield a user from UVC light during operation of the wand.

* * * * *